United States Patent [19]

Teass, Jr.

[11] 4,028,618
[45] June 7, 1977

[54] CIRCUIT FOR MONITORING THE CONDUCTIVITY OF A SOLUTION

[76] Inventor: Horace A. Teass, Jr., 36 Highland Terrace, Pleasantville, N.Y. 10570

[22] Filed: Jan. 9, 1976

[21] Appl. No.: 647,884

[52] U.S. Cl. .......................... 324/30 R; 204/195 C
[51] Int. Cl.² ........................................ G01N 27/42
[58] Field of Search ............. 324/30 R, 30 B, 71 R; 204/195 R, 195 C

[56] References Cited

UNITED STATES PATENTS

| | | | |
|---|---|---|---|
| 3,203,240 | 11/1966 | Spady | 324/30 B |
| 3,493,857 | 2/1970 | Silverman | 324/30 B |
| 3,566,233 | 2/1971 | Kahn | 324/71 R |
| 3,657,640 | 4/1972 | Jelinek | 324/30 B |
| 3,717,566 | 2/1973 | Wilson | 204/195 C |
| 3,924,175 | 12/1975 | Wilson | 324/30 R |

Primary Examiner—Rudolph V. Rolinec
Assistant Examiner—Michael J. Tokar
Attorney, Agent, or Firm—Peck & Peck

[57] ABSTRACT

A circuit for monitoring the conductivity of a solution has a four probe conductivity cell which is supplied by a constant current source to provide a signal proportional to the conductivity. A thermistor is connected in the feedback circuit of an operational amplifier and responds to temperature changes in the solution to change the gain of the amplifier and maintain the circuit output at a predetermined level.

3 Claims, 1 Drawing Figure

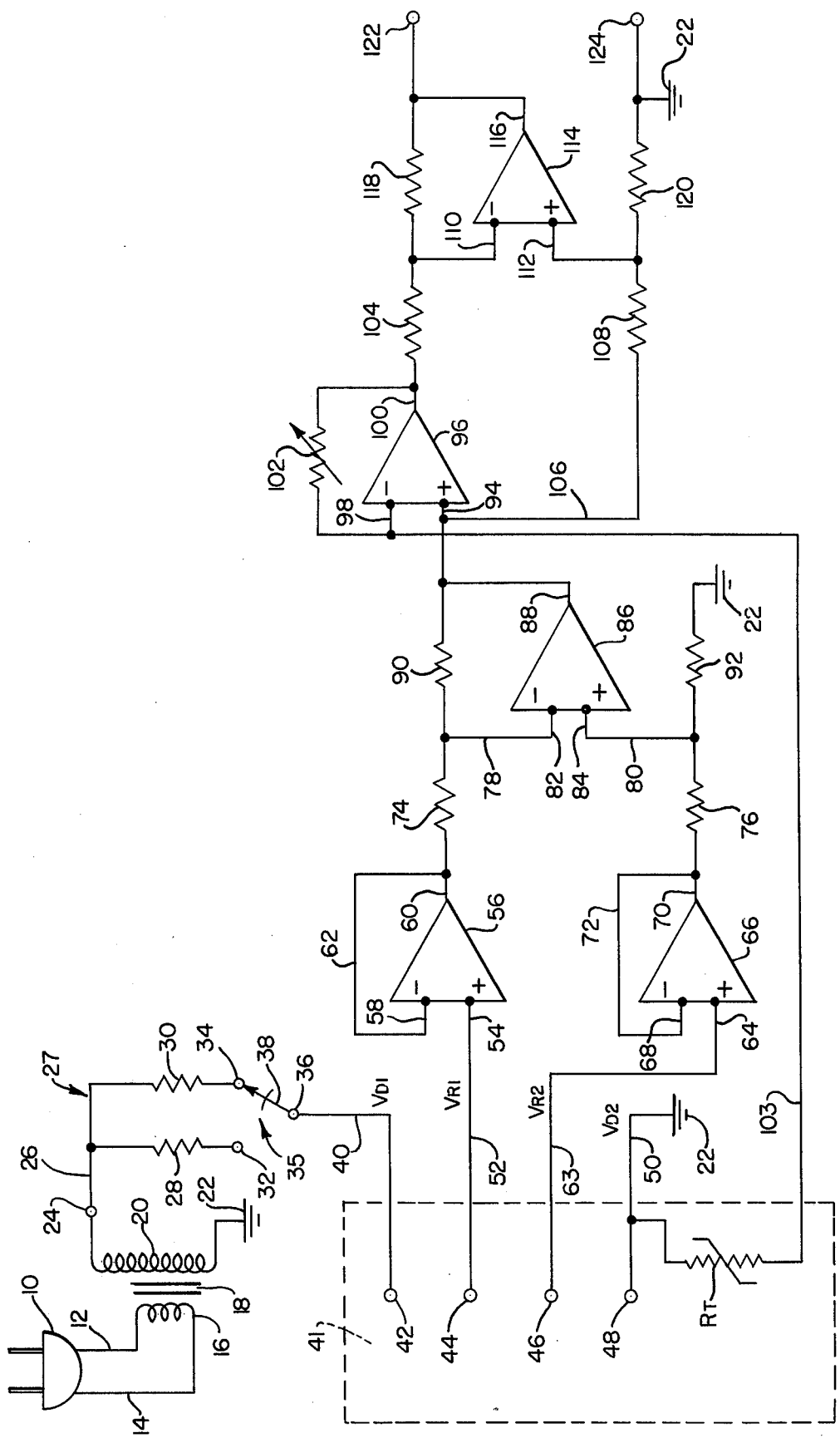

CIRCUIT FOR MONITORING THE CONDUCTIVITY OF A SOLUTION

BACKGROUND OF THE INVENTION

The present invention relates generally to monitoring systems and, more particularly, to a circuit useful for measuring the ionic content of solutions.

The techniques for measuring the ionic content of water are properly divided according to the purity of the water; that is, whether the water is pure or impure. Each division has its own set of problems such that measurement techniques optimized for pure water monitoring are not suitable for impure water monitoring.

In the past two-element conductive probes have been used successfully in pure water situations because the inherent metal-to-water interface resistance is sufficiently masked by the high resistance found in pure water, so as to be negligible. However, as the water purity decreases, there comes a water purity level at which the interface resistance exceeds the allowable error, and other techniques must be utilized.

Prior art systems have attempted to solve the problem noted above by using magnetic and comparative measurement and four-terminal techniques. These solutions have been only partially successful because of limitations of error imposed by their character and/or the systems have been increasingly more complex so as to impose higher cost to achieve low measurement error. However, when the problem is viewed from the aspect of minimum cost versus accuracy, the double or four probe conductivity cell has the most promise.

SUMMARY OF THE INVENTION

Accordingly, it is an object of the present invention to provide a circuit for measuring low to very low specific resistance or ultra high conductivity of solutions.

It is a further object of this invention to provide a double or four probe cell ionic content measuring system which achieves a high degree of accuracy at a minimum of cost.

The present invention is summarized in that a conductivity measuring system includes a four probe conductivity cell divided into two driving probes, which are supplied by a constant current source, and two receiving probes; high input impedance elements connect each receiving probe to a differential circuit which produces a signal proportional to the resistance and conductivity of the solution; a thermistor is connected in the feedback circuit of an amplifier and responds to temperature changes in the solution to change the gain of the amplifier to maintain the circuit output at a predetermined level.

BRIEF DESCRIPTION OF THE DRAWING

The drawing is a schematic circuit diagram of the preferred embodiment of the invention.

DESCRIPTION OF THE PREFERRED EMBODIMENT

The present invention is embodied in a monitoring or measuring system illustrated schematically in the drawing. A source of electrical power (not shown) is connected through plug 10 and conductors 12 and 14 to the primary winding 16 of a transformer 18. The transformer secondary 20 is connected at one terminal to circuit common 22 and at its other terminal to conductor 26 at junction 24. The elements thus far described combine to conveniently provide the proper AC voltage at junction 24, while isolating the remainder of the circuit from the power source.

The invention includes a ranging section, indicated generally at 27, the purpose of which is to selectively vary the magnitude of the AC input signal to the conductivity cell 41. Ranging resistors 28 and 30 are connected between function 24 and terminals 32 and 34, respectively, to range selector switch 35. Switch arm 38 is connected at function 36 to conductor 40, which connects to a conductivity cell, indicated generally at 41. The resistance of the ranging resistors 28 and 30 are chosen to be significantly higher than those of the conductivity cell probes so as to be equivalent to a constant current source in the conductivity ranges of the water to be measured.

The conductivity cell of this measuring system is indicated generally at 41, and includes drive probes 42 and 48, and receiving probes 44 and 46, all of which are designed for immersion into, and direct electrical contact with, the liquid to be measured. Drive probe 42 is connected through conductor 40 to the AC constant current source, and the voltage on it is designated VD1. Drive probe 48 is connected through conductor 50 to circuit common 22. An electrical path is formed between drive probes 42 and 48 through the liquid to be measured. Spaced along this electrical path at the receiving probes 44 and 46; probe 44 is physically closest to drive probe 42 and has a voltage thereon designated as VR1. Probe 46 is physically closest to drive probe 48 and has a voltage thereon designated as VR2. Because of the cell's configuration, VR1 is thought of as always being greater than VR2.

Also included in the conductivity cell 41 is a thermistor RT, which is positioned to be in thermal contact with the liquid to be measured. In general the resistance tracking value of the thermistor approximates that of the liquid under measurement; specific selection of a thermistor depends upon the subject liquid as is well known to those experienced in the liquid conductivity measuring field.

Receiving probe 44 is connected through conductor 52 to the noninverting input 54 of operational amplifier 56, while the amplifier inverting input 58 is connected through conductor 62 to amplifier output 60. Operational amplifier 56 is connected to an appropriate power source (not shown) as is well known.

Receiving probe 46 is connected through conductor 63 to the noninverting input 64 of operational amplifier 66, while the amplifier inverting input 68 is connected through conductor 72 to amplifier output 70. Operational amplifier 66 is connected to an appropriate power source (not shown).

Operational amplifiers 56 and 66 are connected in high impedance follower modes by virtue of the connections between their inverting inputs and their outputs. These modes of operation produce high resistance isolation for the receiving probes 44 and 46. Consequently, a very minimum of current flows in conductors 52 and 63, causing minimum voltage drop at the liquid-probe interface barriers of probes 44 and 46, and resulting in the desired condition that VR1 and VR2 truly reflect the voltage in the liquid and hence its conductivity.

The contact resistances of the drive probes 42 and 48 do not effect the measurement of the liquid's conductivity. In general the liquid's conductivity will vary thereby causing the voltage across drive probes 42 and 48 to vary as a result of their being fed by a constant current source. For example, an increase in the liquid's conductivity will cause a decrease in the voltage across the drive probes; however, the contact resistance of the drive probes is not measured. The receiving probes 44 and 46 respond only to the liquid's conductivity, and interface resistances of the drive probes are swamped-out by the value of ranging resistors 28 or 30, and thus do not distort the VR1 and VR2 relationships.

The invention further includes a differential circuit which discriminates against unwanted signals while faithfully handling voltage differentiation for proper voltages generated by the cell 41. An operational amplifier 86 has an inverting input 82 which is connected through conductor 78 and resistor 74 to amplifier 56 output 60. The noninverting input 84 of amplifier 86 is connected through conductor 80 and resistor 76 to amplifier 66 ouput 70. The inverting input 82 is connected through resistor 90 to amplifier output 88. The noninverting input 84 is connected through resistor 92 to circuit common 22. Operational amplifier 86 is connected to an appropriate power source (not shown).

To insure the best operating results from amplifier 86, the resistor pairs 74 and 76 and 90 and 92 must be closely matched. In operation, the voltages VR1 and VR2, which appear on the receiving probes 44 and 46, are processed through amplifiers 56 and 66 and appear at the inputs of amplifier 86. Amplifier 86 operates to subtract VR2 from VR1 and produces on output 88 a voltage which is the difference between the voltages appearing on receiving probes 44 and 46, which are caused by current flowing through the liquid.

In its preferred embodiment, the invention includes automatic temperature compensation which operate to negate the effects of temperature variations of the liquid under measurement. An operational amplifier 96 has a noninverting input 94, an inverting input 98 and an output 100. Noninverting input 94 is connected to the output 88 of amplifier 86. Output 100 is connected through a resistive voltage divider network comprising variable resistor 102, conductor 103, thermistor RT and conductor 50 to circuit common 22. Inverting input 98 is connected at the junction of resistor 102 and thermistor RT. Amplifier 96 is connected to an appropriate power source (not shown). As is well known, a thermistor is a resistor whose resistance changes as a function of its temperature.

In accordance with well known principles, the functioning of an operational amplifier is defined by the equation:

$$Vo/Vin = Rf/Rin$$

where
Vin = input voltage
Vo = output voltage
Rin = input impedance and
Rf = feedback impedance.

Rearranging the above equation to solve for Vo, it is seen that changes in the feedback impedance can be used to change the gain of the amplifier:

$$Vo = Vin \times (Rf/Rin)$$

As the operating conditions under which the present invention is used change, variations in ambient temperature conditions will cause changes in the conductivity of the liquid, and consequently, changes in the voltages which appear at receiving probes 44 and 46 and at the output 88 of amplifier 86. The temperature compensation system of the present invention automatically compensates for the ambient temperature effects on the liquid by varying the gain of amplifier 96. This gain variation is accomplished automatically by the varying resistance ratio between RT and resistor 102, i.e., changing the feedback impedance of amplifier 96.

For example, consider the situation arising when the liquid's temperature increases. The temperature and conductance of the thermistor RT will increase, as will the liquid's conductivity, resulting in lower voltages VR1 and VR2 appearing at receiving probes 44 and 46, and, consequently, at output 88 of amplifier 86. However, the resistance ratio between thermistor RT and resistor 102 will be increased, resulting in a relative increase in the feedback resistance and gain of amplifier 96, so as to maintain the voltage at output 100 of amplifier 96 at the same value it was before the temperature shifted. Likewise, should the liquid's temperature decrease, the gain of amplifier 96 is automatically increased to compensate for the decrease in voltage output from amplifier 86. Normally, either 20° or 25° are selected as the temperature reference points and the system is adjusted accordingly.

An additional novel feature of the invention permits the temperature compensation means to properly track the changes produced by ambient temperatures. The temperature compensation tracking feature comprises an operational amplifier 114 having inverting 110 and noninverting 112 and an output 116. Inverting input 110 is connected through resistor 104 to output 100 of amplifier 96. Noninverting input 112 is connected through resistor 108 to the noninverting input 94 of amplifier 96. Output 116 is connected through resistor 118 to inverting input 110. Additionally, noninverting input 112 is connected through resistor 120 to circuit common 22. Resistor pairs 104 and 108 and 118 and 120 preferably are closely matched. Amplifier 114 is connected to an appropriate power supply (not shown).

The connection of amplifier 114 across amplifier 96 serves to remove the gain of 1 which would otherwise off-set the temperature compensation, rendering it less than satisfactory. Operational results show that this feature brings the compensation error down to one-fifth of what it would otherwise be.

The ouput across terminals 122 and 124 is directly proportional to the liquid's resistance and inversally proportional to its conductivity. A detection system (not shown) may be connected across terminals 122 and 124 to convert the AC signal to a signal suitable for driving a meter or level detectors for an alarm set point or any of a number of other monitoring or measuring means.

It can thus be seen that the present invention provides a novel system for measuring the ionic content of solutions.

Inasmuch as the present invention is subject to many variations, modifications and changes in detail, it is intended that all matter contained in the foregoing description or shown in the accmpanying drawing shall be interpreted as illustrative and not in a limiting sense.

What is claimed is:

1. A circuit for monitoring the conductivity of a solution comprising:

a conductivity cell having first and second drive probes and first and second receiving probes;

a constant current source connected to said first and second drive probes for supplying current thereto;

a first high impedance voltage follower amplifier connected at its input to said first receiving probe and having an output;

a second high impedance voltage follower amplifier connected at its input to said second receiving probe and having an output;

a differential amplifier having first and second inputs and an output for producing a signal proportional to the resistance and conductivity of said solution, said first input being connected to said first voltage follower output and said second input being connected to said second voltage follower output;

an operational amplifier having inverting and noninverting input being connected to said differential amplifier output;

sensing means responsive to temperature changes in said solution for producing a variable impedance; and, feedback means for said operational amplifier including said sensing means connected between said operational amplifier inverting input and said second drive probe, whereby said operational amplifier responds to said variable impedance for maintaining said signal at a predetermined level.

2. The invention as recited in claim 1 further comprising a variable resistance, wherein said sensing means comprises a thermistor, and wherein said feedback means comprises said variable resistance connected between said operational amplifier output and said inverting input and said thermistor is connected between said inverting input and said second drive probe.

3. The invention as recited in claim 2 further comprising a second operational amplifier having first and second inputs and an output, said first input being connected to said first operatinal amplifier ouput and said second input being connected to said noninverting input.

* * * * *